United States Patent [19]

Wegman

[11] Patent Number: 5,589,171
[45] Date of Patent: Dec. 31, 1996

[54] TREATMENT OF DUPUYTREN'S DISEASE WITH COLLAGENASE

[75] Inventor: Thomas L. Wegman, North Merrick, N.Y.

[73] Assignee: Advance Biofactures of Curacao, Brievengat, Netherlands Antilles

[21] Appl. No.: 294,097

[22] Filed: Aug. 22, 1994

[51] Int. Cl.$^6$ .................................................. A61K 38/48
[52] U.S. Cl. ................................................. 424/94.67
[58] Field of Search ........................................... 424/94.67

[56] References Cited

U.S. PATENT DOCUMENTS

| | | | |
|---|---|---|---|
| 3,678,158 | 7/1972 | Sussman | 424/94.67 |
| 4,174,389 | 11/1979 | Cope | 424/94.67 |
| 4,338,300 | 7/1982 | Gelbard | 424/94.67 |
| 4,485,088 | 11/1984 | Chvapil | 424/447 |
| 4,524,065 | 6/1985 | Pinnell | 424/94.2 |
| 4,645,668 | 2/1987 | Pinnell | 424/94.2 |
| 5,173,295 | 12/1992 | Wehling | 424/94.67 |
| 5,279,825 | 1/1994 | Wehling | 424/94.67 |

FOREIGN PATENT DOCUMENTS

| | | |
|---|---|---|
| 2005488 | 1/1994 | Russian Federation . |
| 706090 | 1/1980 | U.S.S.R. . |

OTHER PUBLICATIONS

Bailey et al., Clinical Science & Molecular Medicine 53: 499–502 (1977).
McCarthy, Journal of Hand Surgery 17B:356 (Br 1992).
Murrell G A, An insight into Dupuytren's contracture, 1992; 74, 156–60.
Bromley, L, The collagen changes of Dupuytren's contracture, 1991; 16, 263–6.
Murrell, G A, Scientific comment, Basic science of Dupuytren's disease, Ann. Chir. Main. Memb. Super. 1993; 11, 355–61.
Ryvedik B, Microvascular response to locally injected collagenase, Scand. J. Plast. Reconstr. Surg. 1989; 23, 17–21.
Ryvedik B, Effects of collagenase on nerve tissue, 1985; 10, 562–6.

Primary Examiner—Michael G. Wityshyn
Assistant Examiner—J. Witz
Attorney, Agent, or Firm—Roland Plottel

[57] ABSTRACT

Dupuytren's disease is treated by applying collagenase to the affected palmar fascia.

7 Claims, 3 Drawing Sheets

TREATMENT OF DUPUYTREN'S DISEASE WITH COLLAGENASE

BACKGROUND OF THE INVENTION

Dupuytren's disease (Dupuytren's contracture) of the hand occurs mainly, though not exclusively, in men. It is found more frequently in middle aged and elderly persons, and those with certain chronic illnesses, e.g. diabetes, alcoholism and smoking. The cause is not known.

The disease is characterized by thickening and contracture of the fascia (connective tissue) of the palm, usually progressing to flexion deformities and involvement of one or more fingers. This results from formation of longitudinal cords of indurated fibrous tissue in the palm. A similar lesion sometimes occurs in the foot. In Dupuytren's contracture the ratio of type III to type I collagen is increased, and an increased number of proliferating fibroblasts is found. No effective palliative treatment has been found; severe cases are treated by surgery (fasciotomy or fasciectomy.)

SUMMARY OF THE INVENTION

The consequences of Dupuytren's disease are ameliorated by treatment of the affected fascia with collagenase, by applying it to the surfaces of, or by direct injection of collagenase into, the areas of fibrosis, i.e. the cords, or in early cases the precursor nodules in the fascia, taking care not to injure the underlying flexor tendon. The tensile modulus of the cords is greatly lessened by treatment with collagenase, thus relieving some of the debilitating tension on the fingers.

DETAILED DESCRIPTION

Collagenase is an enzyme that has the specific ability to digest collagen. It is derived commercially from fermentation by *Clostridium histolyticum*, and is purified by a chromatographic technique.

The potency assay of collagenase is based on the digestion of undenatured collagen (from bovine tendon) at pH 7.2° and 37° C. for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

Sterilized lyophilized collagenase powder is available having a minimum assay of 50 ABC units per mg. The assay may range considerably above that from batch to batch, but is taken into account in determining the weight of powder to use with a pharmaceutically acceptable carrier, e.g. normal saline, in preparing a desired concentration for treatment.

Method of treatment and dosage is, of course, a matter of physician judgment and will depend on, inter alia, the extent of the disease and nature of disablement. As guidelines, one may use liquid carriers containing from about 100 ABC collagenase units or less to about 10,000 ABC units or more per ml. One suitable range has been found to be about 300 to about 700 ABC units per ml. Dosage may range from about 100 ABC units or less up to about 7,500 ABC units or more per affected cord or equivalent structure. This may be administered as a single dose, or generally more effective in aliquotes at two or more locations in the lesion(s). A single treatment may be sufficient, or two or more treatments spaced in time, say monthly, may be used, depending upon observed results. Although favorable results will be seen within a few days or weeks, it must be emphasized that complete relief is often not attainable, and some recurrences may be expected.

It is within the skill of the art to select carriers for the collagenase that are pharmaceutically acceptable, including inertness towards the collagenase. Examples are normal saline, aqueous dextran solution, aqueous hetastarch solution. In some instances the physician may prefer a slow release liquid or solid carrier formulation for injection or implantation, in which case the collagenase dosage would usually be somewhat higher than that used in a simple aqueous injection. One can use as carrier fibrin glue, comprising fibrin or fibrin precursors, e.g. fibrinogen plus thrombin; see U.S. Pat. No. 5,279,825. Again, selection of carrier and methods of preparing formulations are within the skill of the art.

BRIEF DESCRIPTION OF THE DRAWINGS

The drawings are microphotographs of 3.5µ thick sections of contractures, magnification 10×10.

EXPERIMENT I

Figure 1:
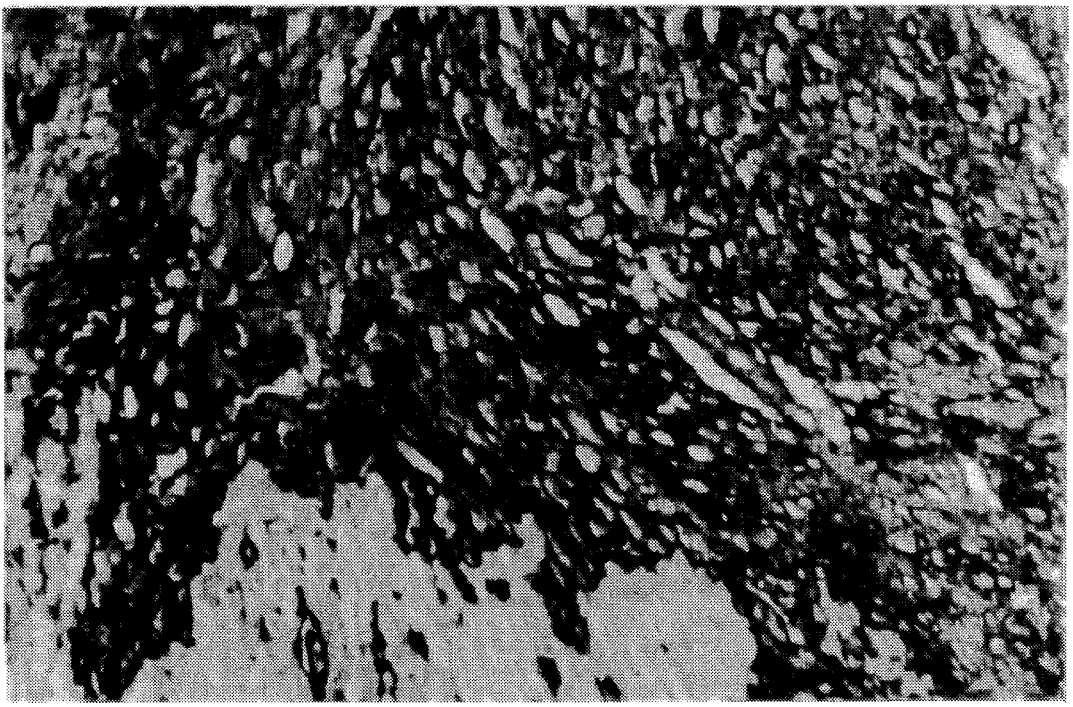
FIG. 1 is a section of a control.

From patients undergoing routine fasciectomy for Dupuytren's disease, twenty excised cords were obtained. The specimens were frozen within 30 minutes following surgery. Ten specimens were randomly assigned to be the control group, and ten were randomly assigned to be treated. After the latter were injected with collagenase, both groups were incubated at 37° C. for 24 hours. The specimens were handled using sterile technique.

Lyophilyzed collagenase powder from Advance Biofactures Corp. of Lynbrook, N.Y. 11563 was reconstituted with a diluent consisting of water, 0.9% NaCl and 2 mmolar $CaCl_2$. Collagenase concentration was 3,600 ABC units per 0.5 ml. This solution was injected as a single dose of 0.5 ml so that each treated cord received 3,600 units collagenase.

Once prepared the specimens were mechanically tested using a Chatilion UTSE-2 machine, which applies strain, i.e. longitudinal pull, in order to determine changes in tensile modulus after application of collagenase. The investigator made two marks on the cords with a pen in order to assess the actual length changes (i.e. strain) the tissue incurred. Anchoring clips were attached near the ends of a cord, and the cord was then inserted into specimen clamps, one on each end. The clamps were attached to the Chatilion-2 UTSE machine, which then applied the strain. A 12.5× microscope observed the distance between the marks and the observations were subjected to computer aided video analysis.

The mean tensile modulus for the collagenase treated group was decreased by a factor of 15: mean tensile modulus in the control group was 33.0169 MPa (std. deviation +/−22.9386 MPa), as compared to 2.1653 MPa (std. deviation +/−3.2027 MPa) for the treated group ($p<0.002$).

Histologic examination of the treated group revealed evidence of collagen bundle disruption. This was not found in the control group.

Thus, treatment with collagenase is highly effective at disrupting, and reducing the tensile modulus of, the pathologic cord in Dupuytren's disease, with consequent reduction of the debilitating tension on the fingers.

EXPERIMENT II

The patients of Dupuytren's contracture came to the hand surgery division of the hospital for operation. The contracture was removed and placed, wrapped in moist compresses, in an unmarked jar.

The jar was brought to the laboratory where the contracture was cut clean of fat, etc., so that only diseased tissue remained. Then the contracture was cut into four pieces of approximately the same size. Three of the pieces were placed in Eppendorf's centrifuge tubes, 1.5 ml.

Collagenase is an enzyme which breaks down the peptide bonds in the protein collagen. Collagen is also found in the skin, so that it is important to wear gloves.

The required number of containers of collagenase (freeze-dried Nucleolysin® which is collagenase purified by a chromatographic technique, supplied by Advance Biofactures Corp., Lynbrook, N.Y. 11563), was taken out of the freezer, where they were kept, and reconstituted in diluent consisting of water, NaCl (Baxter's NaCl for injection, 9 mg/ml) and $CaCl_2$ (Merck's pulver purum, anhydrous), and contained 0.9% sodium chloride and 10% calcium chloride.

Each container of Nycleolysin® contained 810 ABC units (U) collagenase. To each was added the volume of diluent required to provide one of the following concentrations:

225 U/ml

450 U/ml

600 U/ml

675 U/ml

900 U/ml

The contents of each container of reconstituted Nycleolysin® was used to coat two of the pieces of a contracture. The third piece was coated with diluent. Then the three jars were placed in an incubator for incubation at 37° C. for 48 hours. The remaining piece was used as control and was not incubated.

After incubation the pieces were placed, together with the untreated control piece, in formaldehyde (Apoteksbolaget's buffered neutral 4% formaldehyde for technical use), before fixation for at least one 24-hour period. After fixation, the pieces were dehydrated on the following schedule:

| Dehydration Schedule | | |
|---|---|---|
| ◆ 70% Alcohol | | overnight |
| ◆ 96% Alcohol | one piece | two hours |
| ◆ Absolute alcohol | two pieces | three hours |
| ◆ Xylene | | 30–45 min |
| ◆ Paraffin | on hotplate | app. 19 hours. |

These specimens imbedded in paraffin were sectioned using a rotary microtome (LKB 2218 Historange Microtome), cutting the pieces into sections 3.5μ thick. After that, the section was stained by two methods in order to visualize any possible reduction of collagen. Van Gison's solution, a specific stain for connective tissue, was used as a general staining method. The Masson trichrome stain, a specific method for collagen, was used as a more specific method for indicating collagen directly.

Figure 2:
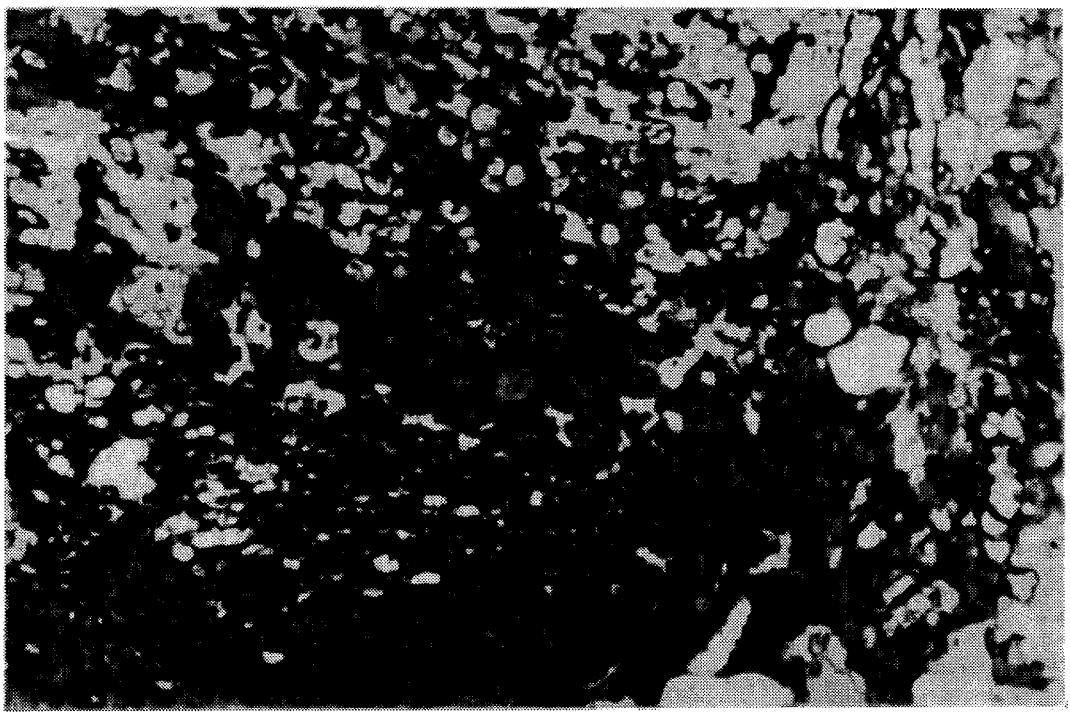
FIGS. 2 is a section of sample treated with diluent only.

Examination of the sections which were made of the incubated material revealed that control (FIG. 1) and diluent control (FIG. 2) had approximately equally large quantities, and equally little dissolved, collagen. The collagen lay in large islands, which appeared thick and indurated and were heavily stained. The collagen was not broken up.

Figure 3:
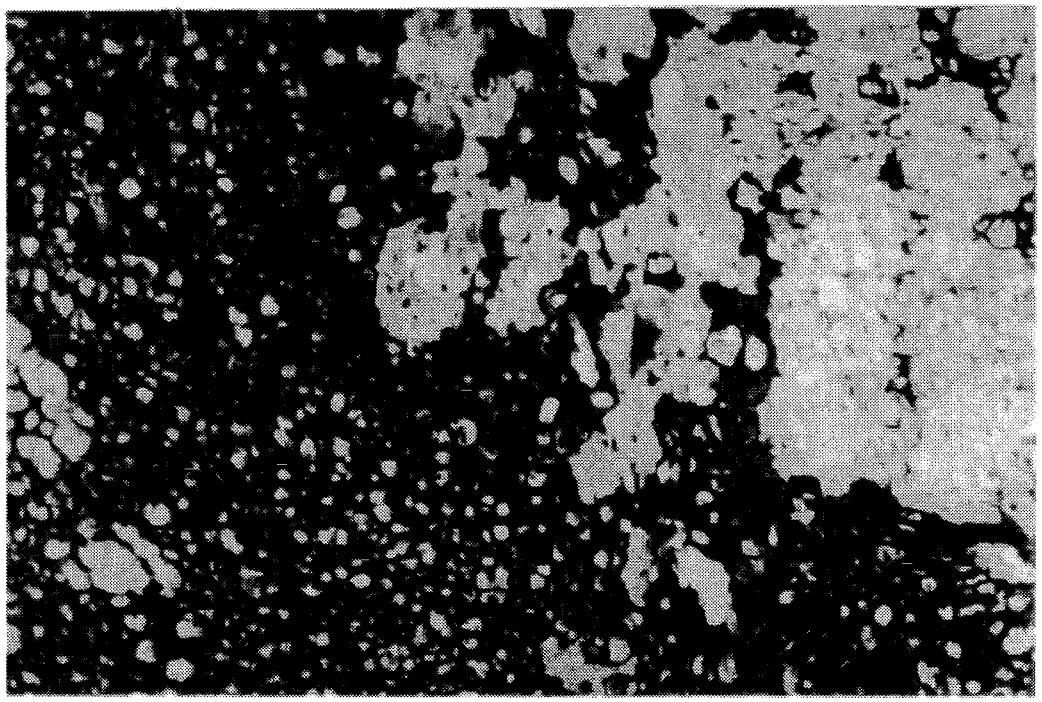
FIG. 3 is a section of sample incubated with 225 ABC units (U) collagenase/ml.

In the section that was collagenase-treated with 225 U/ml, the collagen appeared intact in large chunks, while at the same time seeming to be broken up at certain spots. (FIG. 3).

Figure 4:
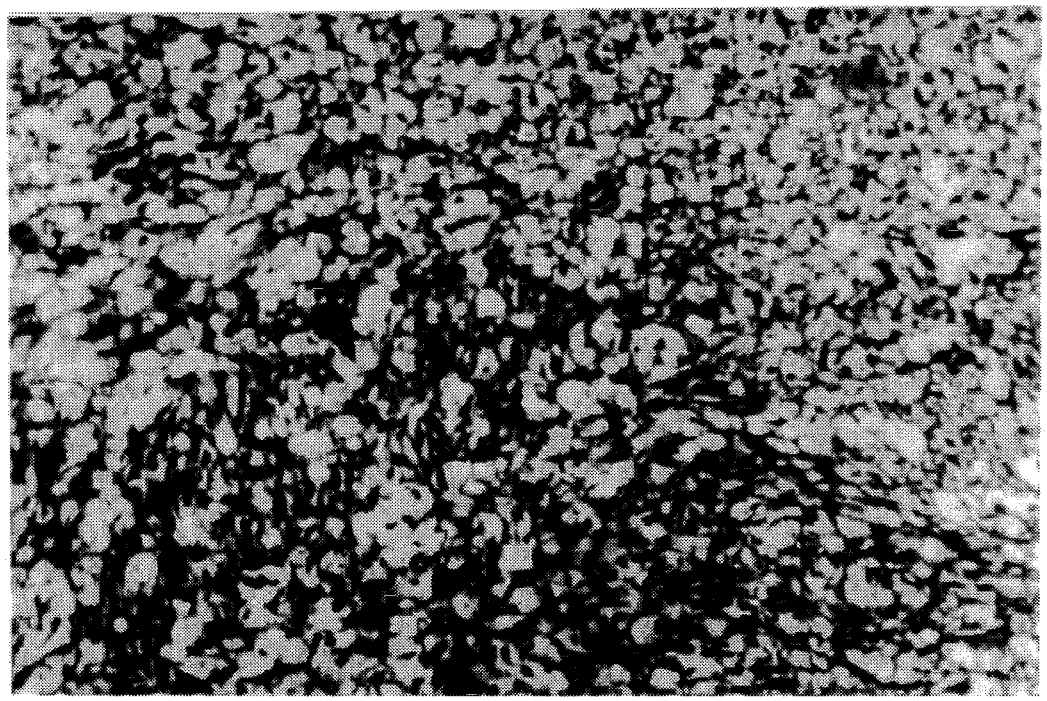
FIG. 4 is a section of sample incubated with 450 U/ml.

Examination of the section which was made after incubation in 450 U/ml collagenase solution revealed that the collagen was distinctly thinned, and that the collagen formed a network. (FIG. 4)

Figure 5:
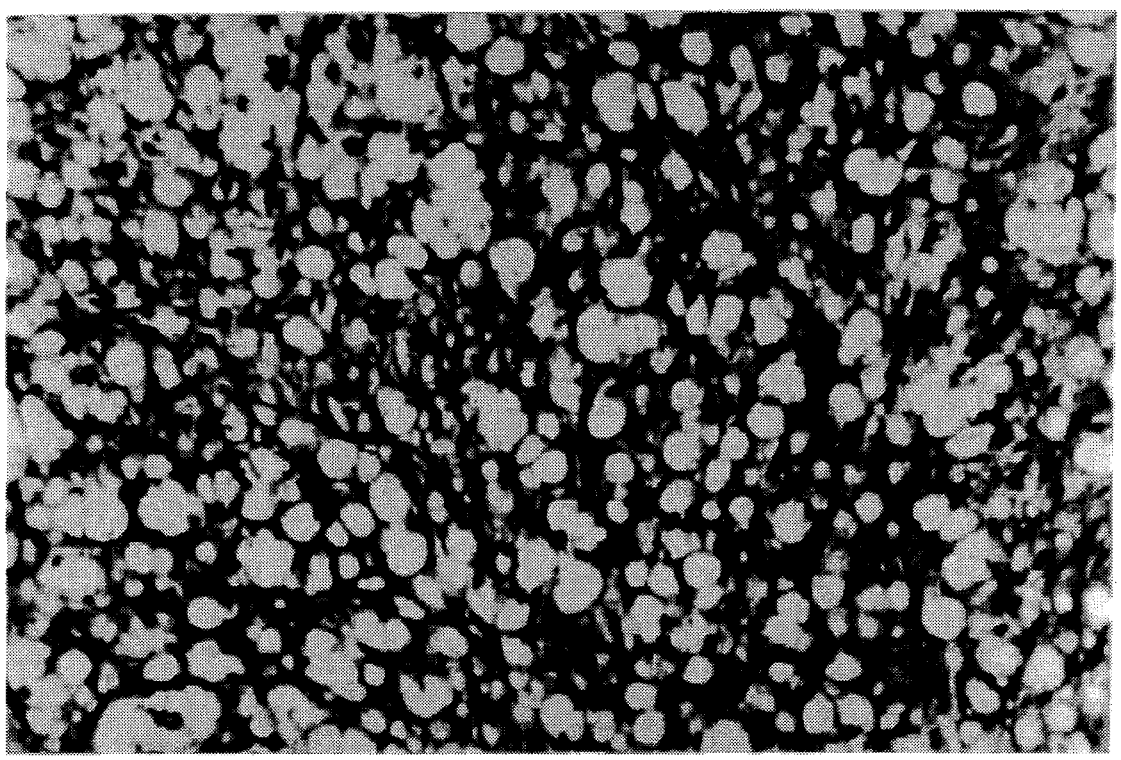
FIG. 5 is a section of sample incubated with 675 U/ml.

In the section made after treatment with 675 U/ml collagenase, it could be clearly seen that the collagen network was very much broken up and the collagen could now begin to soften. (FIG. 5).

Based on examination of the sections, at these test conditions 450 U/ml appeared to be a suitable concentration since it dissolved the collagen somewhat, but not so much that there seems to be any risk of injury to the flexor tendons.

Bibliography (1) Gold B A, Treatise on Collagen volume 2, 2nd ed. London: Academic Press, 1968.

(2) Murell G A, An insight into Dupuytren's contracture, Ann. R Coll. Surg. Engl. 1992; 74, 156–60.

(3) Bromley L, Murell G A, Francis M J. The collagen changes of Dupuytren's contracture, J. Hand. Surg. Br. 1991; 16, 263–6.

(4) Murrell G A, Scientific comment, Basic science of Dupuytren's disease, Ann. Chir. Main. Memb. Super. 1993; 11, 355–61.

(5) Fleishmajor R, Kühn K, Olsen B R, Biology, chemestry and pathology of collagen, Annals of the New York academy of sciences, volume 460. New York: 1985.

(6) Weiss J B, Jayson M T V. Collagen in health and disease, 2nd ed. London: Churchill Livingstone, 1982.

(7) Sobotta, Becher, Atlas der deskriptiven Anatomie des Menschen, Munchen-Berlin: Urban & Schwarzenberg, 1964.

(8) Burgeson R E, Mayne R. Structure and function of collagen types, 2nd ed. London: Academic Press, 1987.

(9) Mandl J. Collagenase, London: Gordon and Breach science publishers, 1972.

(10) Structure, molecularbiology and pathology of collagen, Annals of the New York academy of sciences, volume 580. New York: 1985.

(11) Brown M D, Intradiscal therapy, London: Year book medical publishers, 1983.

(12) Bancroft J D, Stevens A. Theory and practice of histological techniques, 3rd ed. London: Churchill Livingstone, 1990.

(13) Ryvedik B, Ehira T, Olmarker K et al. Microvascular response to locally injected collagenase, Scand. J Plast. Reconstr. Surg. 1989; 23, 17–21.

(14) Ryevik B, Brown M, Ehira T et al. Effects of collagenase on nerve tissue, Spine 1985; 10, 562–6.

(15) Wehling P. Method of enhancing the regeneration of injured nerves and adhesive pharmaceutical formulation therefor, U.S. Pat. No. 5,279,825, 1994.

I claim:

1. A method of treating an individual suffering from Dupuytren's disease which comprises applying an effective amount of collagenase to a fibrous of the affected fascia.

2. A method according to claim 1 wherein the amount of collagenase is within the range of about 100 to about 7,500 ABC units.

3. A method according to claim 1 wherein the collagenase is applied in a pharmaceutically acceptable carrier in a concentration of about 100 to about 10,000 ABC units collagenase per ml.

4. A method according to claim 3 wherein the concentration of collagenase is within the range of about 300 to about 700 ABC units per ml.

5. A method according to claim 3 wherein the carrier is aqueous.

6. A method according to claim 1 wherein the collagenase is applied to the fibrous cord.

7. A method according to claim 6 wherein collagenase in a liquid pharmaceutically acceptable carrier is injected into the fibrous cord.

* * * * *